(12) United States Patent
Linderman

(10) Patent No.: US 10,008,126 B1
(45) Date of Patent: Jun. 26, 2018

(54) TRAINING AID FOR COMPLEX ATHLETIC MOVES

(71) Applicant: Michael Linderman, Ogdensburg, NY (US)

(72) Inventor: Michael Linderman, Ogdensburg, NY (US)

(73) Assignee: Marina Linderman, Ottawa (CA)

( * ) Notice: Subject to any disclaimer, the term of this patent is extended or adjusted under 35 U.S.C. 154(b) by 344 days.

(21) Appl. No.: 14/994,138

(22) Filed: Jan. 12, 2016

Related U.S. Application Data

(63) Continuation-in-part of application No. 14/949,851, filed on Nov. 23, 2015, which is a continuation of application No. 13/861,441, filed on Apr. 12, 2013, now Pat. No. 9,192,335.

(60) Provisional application No. 62/141,301, filed on Apr. 1, 2015.

(51) Int. Cl.
| | |
|---|---|
| *G09B 19/00* | (2006.01) |
| *A61B 5/0488* | (2006.01) |
| *A63B 24/00* | (2006.01) |
| *A61B 5/00* | (2006.01) |

(52) U.S. Cl.
CPC ........ *G09B 19/0038* (2013.01); *A61B 5/0488* (2013.01); *A61B 5/6825* (2013.01); *A61B 5/742* (2013.01); *A63B 24/0006* (2013.01); *A61B 2505/09* (2013.01); *A63B 2024/0012* (2013.01)

(58) Field of Classification Search
CPC ........ A63B 24/0006; A63B 2024/0009; A63B 2024/0012; A63B 2024/0015; A61B 2505/09; A61B 5/0448; G09B 19/0038
See application file for complete search history.

(56) References Cited

U.S. PATENT DOCUMENTS

| | | | | |
|---|---|---|---|---|
| 6,076,011 A | * | 6/2000 | Hoover | A61B 5/0488 600/546 |
| 8,280,503 B2 | * | 10/2012 | Linderman | A61B 5/0488 434/155 |
| 8,348,862 B2 | * | 1/2013 | Chu | A61B 5/0488 473/219 |
| 2013/0244211 A1 | * | 9/2013 | Dowling | G06F 19/3481 434/247 |

(Continued)

FOREIGN PATENT DOCUMENTS

| | | | |
|---|---|---|---|
| JP | 08224330 A | * | 9/1996 |
| JP | 2003339908 A | * | 12/2003 |

*Primary Examiner* — David J McCrosky
(74) *Attorney, Agent, or Firm* — Michael D. Eisenberg

(57) ABSTRACT

A training aid for an athletic movement comprises: an EMG acquisition device for placement on a muscle of a user. The training aid is configured to: identify an acquired set of EMG signals generated during the movement from muscles in two different appendages; divide the set of EMG signals into a sequence of smaller time intervals; compare the placement in the smaller time intervals of peak EMG signals in the acquired set of EMG signals to a reference criteria; identify whether the acquired EMG signals satisfy or does not satisfy the reference criteria during the movement. A set of movements are displayed, such that a displayed movement is matched to acquired EMG signals during one of the smaller time intervals, and the movements are displayed with an indication of which move or moves are wrong based on whether the EMG signals matched with the movement, satisfies the reference criteria.

20 Claims, 16 Drawing Sheets

(56) References Cited

U.S. PATENT DOCUMENTS

2017/0027501 A1* 2/2017 Senanayake ......... A61B 5/0488
2017/0112418 A1* 4/2017 Comeau ............... A61B 5/0488

* cited by examiner

TRAINING AID FOR COMPLEX ATHLETIC MOVES

CROSS-REFERENCES TO RELATED APPLICATIONS

This application claims priority from U.S. Provisional Application Ser. No. 62/141,301 filed Apr. 1, 2015, and is a continuation in part of U.S. application Ser. No. 14/949,851 filed Nov. 23, 2015, which is a continuation of U.S. application Ser. No. 13/861,441 filed Apr. 12, 2013, now U.S. Pat. No. 9,192,335, which are each hereby incorporated herein by reference in their respective entirety.

TECHNICAL FIELD

This invention relates to a method, system and apparatus for training a subject in complex athletic movements, and in particular, the golf swing.

BACKGROUND OF THE INVENTION

Golf is a 700 year old sport, popular worldwide. A variety of golf training techniques have been developed over these years. Modern golf training aids utilize computer technologies, video tracking and virtual reality. As the body movements during a golf swing appear to be so complex, golfers always intuitively assumed that if they were able to stabilize the most important moves, their swing would improve. However, since these moves were difficult to track and control, the only criteria for a good golf swing was the resulting trajectory of a golf ball.

Electromyography (EMG) studies of golf have examined activity patterns in the arm, trunk and leg muscles during the execution of strokes (Marta et al. 2012). The majority of these studies were conducted in professional golfers. However, it always remained a mystery of what exactly had to be improved in a golf swing.

The present invention describes the EMG pattern that was discovered in players of different gender, age, and skill level. Surface EMG recordings were employed from intrinsic hand muscles to evaluate the characteristics of the golf grip during the execution of the swing sequence (FIG. 1). Although it is well known that EMG signals are generated during physical activity, these signals were not utilized for the improvement of athletic performance, e.g. a golf swing. Intrinsic muscles of hands can generate a common pattern of EMG during a golf swing. This pattern should be generated, if all elements of the golf swing are performed correctly by a golf player. Indeed, the point of contact of the hands with the club serves as the end effectors during golf strokes. All forces are applied to the golf club through the hands, which makes intrinsic hand muscles very special in this motor task even though many muscles of the body generate the swing. By squaring EMG values of selected hand muscles in both hands over time intervals, a well defined pattern maybe exhibited during the execution of golf swing.

The present invention provides the inside view on important muscle movement in a golf swing, by analyzing the electrical activity of both hands muscles and evaluating movement based on this information. It simply tells a player, which move(s) were wrong. Having this information, the player has to repeat the whole swing again paying close attention to the moves that were marked as wrong, or missing.

Every serious golf player intuitively knows that the outside views of golf swings are incomplete. There is infinite number of ways players can contract or relax their muscles during the movements in a golf swing, even when they are just standing still. No camera would be able to detect their muscle activity. Yet, this type of activity can make a difference in a swing.

The present invention adds very important information to all existing learning methods that are only based on the outside observation. The electrical activity of hand muscles during a golf swing are not sporadic and not even unique to golf players, genders, or age groups. Identified herein is a common pattern of EMG intensities that occurs during a successful golf swing. The successful golf swing is defined as a sequence of controlled moves, causing a ball to end up in a desired location. Different athletes usually place emphasis on using different muscles of the body, while performing a complex move such as a golf swing, chip, putt, drive, etc. The intuitive choice of their style is based on the constitution and development of their body. However, a common pattern of muscle activity of both hands during the golf swing was discovered. In this document, a method of identifying: 1) this pattern, 2) when it is generated and 3) how to translate it into the sequence of hand moves is described. The successful pattern of electrical activity of two muscles in each hand is defined. The appearance of this pattern in the muscles of both hands is a criterion of successfully controlled movements.

The sequence of moves is controlled, if it is possible to find the correspondent move of an athlete for every peak in muscle activity. For example, assuming the sequence of moves as shown in FIG. 1, in order for the moves to be successfully controlled, the system should be able to identify at least four moves from the muscle activity. When professionals successfully swing a golf club, the electrical activity of their hand muscles is very similar and clearly indicates which moves resulted from it. The present invention can extract this information and map it to individual moves according to their position in a sequence of a golf swing. The present invention will help golf players to eliminate their mistakes which cannot be observed from outside.

EMG pattern is not the precise measure of muscles activity, but an approximation. There is some variance of the activity within a pattern. Some combinations of this activity will result in a successful swing. It is a necessary condition for a player to generate the EMG pattern, but not the sufficient condition for a successful swing. For example, even if the EMG pattern was generated, a player can miss the ball. This will not result in a successful swing. Another scenario is, when a player holds the club the wrong way, or under the wrong angle. This swing will not be successful, even if the correct EMG pattern will be generated.

This invention is based on the discovery made by Michael Linderman. Linderman discovered how the fixation of specific movements can generate almost non variant pattern activity in alpha motor neurons during a successful golf swing and the algorithm for translating the EMG peaks into the correspondent hand moves. He also observed the difference with non professional golf students, and inexperienced athletes.

U.S. Pat. No. 9,192,335 discloses a system and method for "Athletic Glove Providing Feedback Regarding Grip to a Wearer". In that patent, a user had differential amplifiers on both hands. Two pairs of differential electrodes were connected to two muscle groups on each hand. Amplified signals were digitized at 1000 Hz sampling rate. Then it was possible to identify the Electromyography (EMG) peaks according to the golf swing sequence shown on FIG. 1. This identification is based on knowing the time of the swing (a user will tap on a screen or otherwise indicate the beginning of a swing) and on synchronization of all four muscle's EMG peaks using the largest peak correspondent to the impact move, i.e. when a golfer is hitting the ball. However, it was not obvious even from the previous disclosure how to make the motor neurons generating the same activity in hand muscles during, for example, such complex athletic movements as in golf, or baseball swing.

BRIEF SUMMARY OF EMBODIMENTS OF THE INVENTION

According to one embodiment of the invention, a training aid for an athletic movement comprises an EMG acquisition device for placement on a muscle of a user and a processor and a computer readable medium, having computer readable instructions stored thereon. The instructions, when read by the processor, cause the processor to: identify an acquired set of EMG signals generated during the movement from muscles in two different appendages; divide the set of EMG signals into a sequence of smaller time intervals; compare the placement in the smaller time intervals of peak EMG signals in the acquired set of EMG signals to a reference criteria; identify whether the acquired EMG signals satisfy or does not satisfy the reference criteria during the movement; and display a set of movements that are matched to the acquired EMG set such that a displayed movement is matched to acquired EMG signals during one of the smaller time intervals, and the movements are displayed with an indication of which move or moves are wrong based on whether the EMG signals matched with the movement satisfies the reference criteria.

In a variant of the training aid, the set of movements comprise a series of movements, that when aligned together in time, comprise the athletic movement with the indication of which of the series movements are wrong based on whether the EMG signals matched with the movement satisfies the reference criteria.

In another variant of the training aid, identifying whether the acquired EMG signals satisfy or does not satisfy the reference criteria during the movement comprises identifying an intensity peak associated with a shorter movement and determining if the time interval of the peak is longer than a predetermined length of time; wherein if the time interval exceeds the predetermined time, the training aid displays an indication of error.

In a further variant, a training aid for completing a golf swing comprises: an EMG acquisition device for placement over a muscle in a hand of a user and a processor and a computer readable medium, having computer readable instructions stored thereon. The instruction, when read by the processor, cause the processor to: identify an acquired pattern of EMG signals generated during the movement; compare the acquired pattern to a reference EMG criteria; and display an indication of whether the acquired EMG pattern satisfies the reference EMG criteria during the movement.

In yet another variant of the training aid, the duration of the golf swing is divided into a sequence of movements, at least some of which are identified by the presence of EMG signal peaks in the acquired EMG pattern.

In still a further variant of the training aid, one of the sequence of movements comprises an impact movement, and the training aid further comprises four EMG acquisition channels configured to acquire EMG signal patterns from two muscles in a dominant hand of the user and two muscles from a non-dominant hand of the user. Comparing the acquired pattern to a reference EMG criteria, comprises: first identifying a largest EMG signal peak acquired from each channel and determining whether the peak in each of the four channels occurred within a predetermined time interval of each other; and if all peaks did not occur within the predetermined time interval, displaying an indication that the EMG pattern failed to satisfy the reference EMG criteria for the impact movement.

In a variant of the training aid, if any of largest EMG signal peaks occurred over a duration longer than a second predetermined time interval, displaying an indication that the EMG pattern failed to satisfy the reference EMG criteria.

In another variant of the training aid, comparing the acquired pattern to a reference EMG criteria, comprises identifying a third EMG signal peak acquired immediately preceding the largest EMG signal peak; and if the third EMG signal peak occurred over a duration longer than a third predetermined time interval, displaying an indication that the EMG pattern failed to satisfy the reference EMG criteria, for a third movement immediately preceding the impact movement.

In a further variant of the training aid, comparing the acquired pattern to a reference EMG criteria, comprises identifying a second EMG signal peak acquired immediately preceding the third EMG signal peak; and if the third peak occurred over a duration longer than a fourth predetermined time interval, displaying an indication that the EMG pattern failed to satisfy the reference EMG criteria, for a second movement immediately preceding the third movement.

In yet another variant of the training aid of claim, comparing the acquired pattern to a reference EMG criteria, comprises identifying a first EMG signal peak acquired immediately preceding the second EMG signal peak, and from a channel configured to acquire EMG signals from the dominant hand of the user; and if the first peak occurred over a duration longer than a fourth predetermined time interval, displaying an indication that the EMG pattern failed to satisfy the reference EMG criteria, for a first movement in the sequence of movements comprising the golf swing.

In still a further variant of the training aid, comparing the acquired pattern to a reference EMG criteria, comprises determining whether a duration of time between the third and fourth EMG signal peaks is shorter than a duration of time between the second and third EMG peaks; if the duration of time between the third and fourth EMG signal peaks is longer than a duration of time between the second and third EMG peaks, displaying an indication that the EMG pattern failed to satisfy the reference EMG criteria, for second, third and the impact movements comprising the golf swing.

In a variant of the training aid, the processor is configured to: compute intensities of the based on acquired EMG signals; divide an entire time of the golf swing into a plurality of smaller equal length time intervals; and compute a mean intensity in each of the plurality of smaller time intervals.

In another variant of the training aid, identifying a third EMG signal peak acquired immediately preceding the largest EMG signal peak, comprises identifying a third EMG signal peak acquired immediately preceding the largest EMG signal peak acquired in the user's non-dominant hand detected from a muscle connected to a thumb.

In a further variant of the training aid, the second EMG signal peak acquired immediately preceding the second EMG signal peak is acquired from the user's non-dominant hand detected from a muscle connected to a thumb.

In still another variant of the training aid, the channel configured to acquire EMG signals from the dominant hand of the user is configured to acquire EMG signals from a muscle connected to a little finger of the dominant hand.

In yet a further variant, a training aid for improving a golf swing, comprises: sensors for measuring electrical activity in muscles of both hands of a user; a processor configured to: divide the electrical activity into a sequence of time intervals; compare peak electrical activity detected by the sensors to a set of reference conditions of electrical activity for a sequence of movements that comprise a golf swing; cause a display device to identify which, if any, of the sequence of movements that comprises the golf swing, failed to meet the reference conditions; and cause the display device to display the set of movements with the indication of which moves were wrong from the point of muscle activities.

In a variant of the training aid, the reference conditions comprise a fourth peak electrical activity in both hands occurring within a predetermined time interval and if the peak electrical activity failed to occur within the predetermined time interval, the processor is configured to display an indication of a failed condition associated with at least one of the sequence of movements.

In another variant of the training aid, the reference conditions comprise locating a third peak electrical activity occurring before the fourth peak electrical activity in a non-dominant hand of a user, and determining whether the third peak occurred over a duration shorter than a second predetermined time interval; if the third peak occurred over a duration longer than the second predetermined time interval, the processor is configured to display an indication of a failed condition for at least one of the sequence of movements.

In a further variant of the training aid, the reference conditions comprise locating a second peak electrical activity occurring before the third peak electrical activity in a dominant hand of a user, and determining whether the second peak occurred shorter than the second predetermined time interval.

In still another variant of the training aid, the reference conditions comprise determining whether a third intensity peak occurred within a predetermined time interval from a center of a maximum peak and the processor is configured to display an indication of a failed condition associated with a movement preceding an impact movement.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
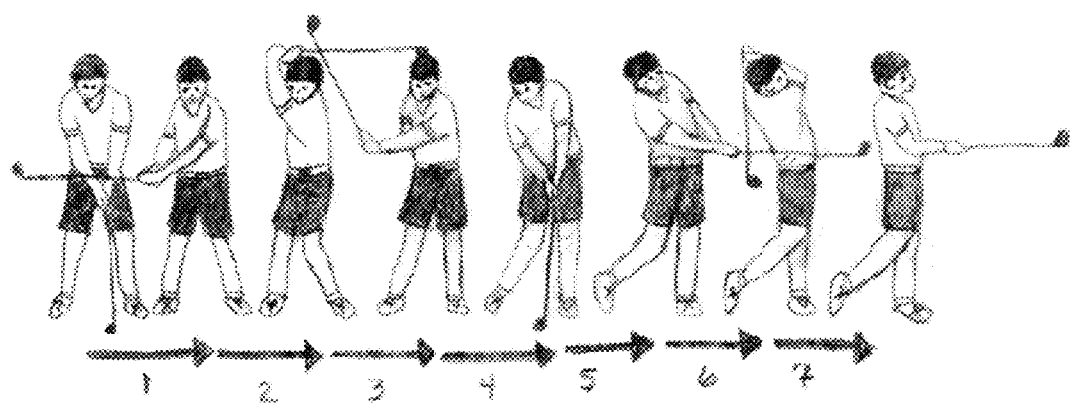
FIG. 1 illustrates a sequence of moves in a golf swing divided into seven movements numbered 1-7.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

The present invention provides a view of the muscle activity involved in movements in a golf swing. It analyzes the electrical activity of hand muscles and evaluates a series of movements based on this information. Then it simply tells a player, which movement(s) in the series was wrong. Having this information, the player can repeat the whole swing again paying close attention to the moves that were marked as wrong, or missing.

Every serious golf player intuitively knows that views just a player's motion of their golf swings present incomplete information about the player's muscle movement during the swing. There is an infinite number of ways players can contract or relax their muscles during the movements in a golf swing and even when they are just standing still. No camera would be able to detect their muscle activity. Yet, this type of activity can make a difference in a swing.

The present invention adds very important information to all existing learning methods that are only based on outside observation (cameras, accelerometers, etc.). Research conducted in connection with the present invention demonstrated that the electrical activity of hand muscles during a golf swing are not sporadic and not even unique to golf players, genders, or age groups. The differences are in the moves of other body parts. When professionals successfully swing a golf club, the electrical activity of their hand muscles is very similar and clearly indicates which moves resulted from it. Computer implemented methods of the present invention, can extract this information and map it to individual moves according to their position in a sequence of a golf swing. It will help golf players to eliminate their mistakes which cannot be observed from outside the player's body.

When athletes see disappointing results, they may think that they are doing everything the same as during another time, when they were happy with the results. Outside observation will not tell one how long and how hard the athlete gripped the golf club using different areas of hands in order to make each move. Only the combined activity of two hand muscles reveals if the moves were executed correctly and synchronously. A method of the present invention assumes that the athlete is given detailed instructions on the general sequence of moves and the technique for each move. This information is generally available. The present invention provides information on whether the moves were executed correctly by hand muscles.

Figure 13:
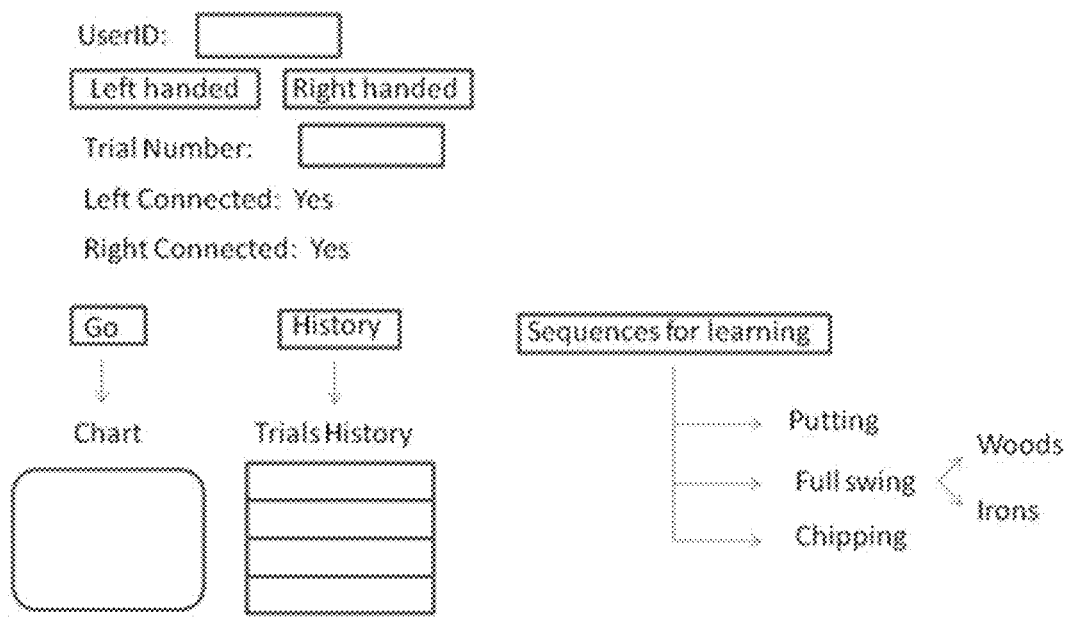
FIG. 13 illustrates a user interface on a computer device.

One embodiment of the training aid for complex athletic moves illustrated herein includes a method and system for a golf improvement system and user interface (GUI) for stationary computer device, a mobile or wearable device, such as smart phone, laptop, and body mounted display, etc. Referring to FIG. 13, a GUI allows users to record golf swings with a unique user ID and a time stamp. The system is configured to report proper connections for electrodes in left and right hands and that connections between a mobile device and electronic boxes on right and left hands are established. After pushing a "Go" button (a player is also notified by voice or audio and starts performing the serious of moves), the system starts acquiring the EMG signals. As soon as this button is pushed, either by someone else who is standing beside a user or a user himself, the user commences swinging a golf club. Next, the Go button changes color to green, as an indication that the system is acquiring and sending the data to a mobile device. After this process is done, a sequence of moves in a swing are displayed on a screen of a computer device with indicators of which moves were in error, as illustrated in FIG. 14.

Figure 14:
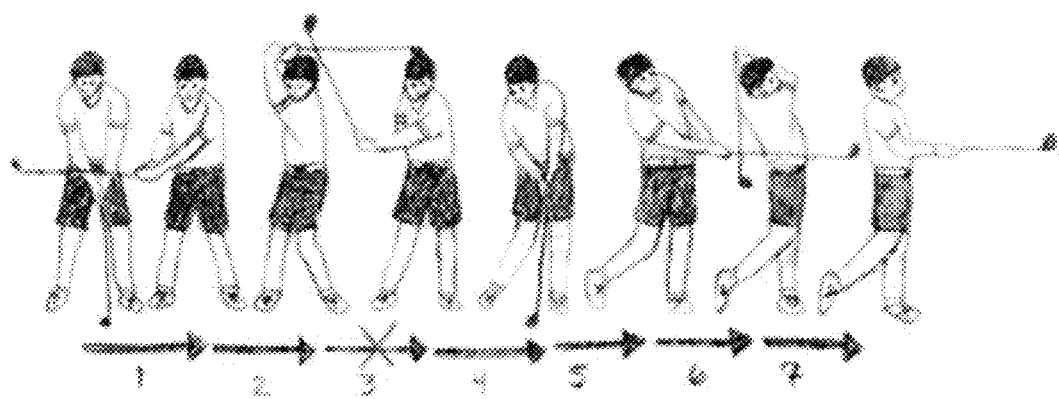
FIG. 14 illustrates a golf swing sequence showing that move 3 was in error.

Users are able to see the result of their swing displayed as a pictorial representation of a particular move that was in error, for example, as illustrated in FIG. 14, rather than a chart containing EMG signals. Selecting the picture having an indicator of an error, such as an X on an arrow, results in a moving avatar or a short video clip opened as a new window to show the correct move in slow motion. Optionally, a graphical representation of left and right hands is presented with indicators on the specific hand and part of the hand where the muscle was flexed for too long or short or too hard or soft. The user practices the complete golf swing paying special attention to the movement that needs to be corrected. Thus, the present invention captures a mistake in the motor neuronal activity that happened at a very high speed of the whole body movements during the swing, and show this mistake to a user in a familiar form of a movement in question. The correct EMG pattern is generated, when an athlete makes all hand moves in a sequence of a swing. The program can evaluate the pattern by analyzing EMG peaks in all channels.

Golfers generally underperform for two reasons: (1) they do not have accurate information on how exactly the correct move has to be performed; and (2) they do not have accurate feedback from their hand muscles that shows them what exactly they have done wrong with their hands. This is information internal to the hands that cannot be observed from the outside, even using a camera. The present invention captures the bio electrical activity of hand muscles (EMG) and matches them to their respective hand movements. The information about the hand movement that was obtained directly from the translation of hand muscles EMG adds extra accuracy to the description of a complex movement such as for example a golf swing. The absence of this extra accurate feedback leads to unacceptably high variability of a golf swing. A user will see all the moves, accurate and inaccurate, in a sequence after the translation is made.

By pressing a button labeled, History, a user causes the system to display a list of recorded trials representing individual swings. The trials may be in a list according to user IDs and date time stamps. A user can go into individual trials and look at their mistakes, or delete individual trials and all trials.

By pressing a button labeled, Sequences for learning, a user can cause the system to bring up a screen showing sequences of moves for putting, full swing with woods or irons, or chipping. Every move is illustrated in detail by an animated figure, such as an avatar, or a video of a real golf player.

Figure 3:
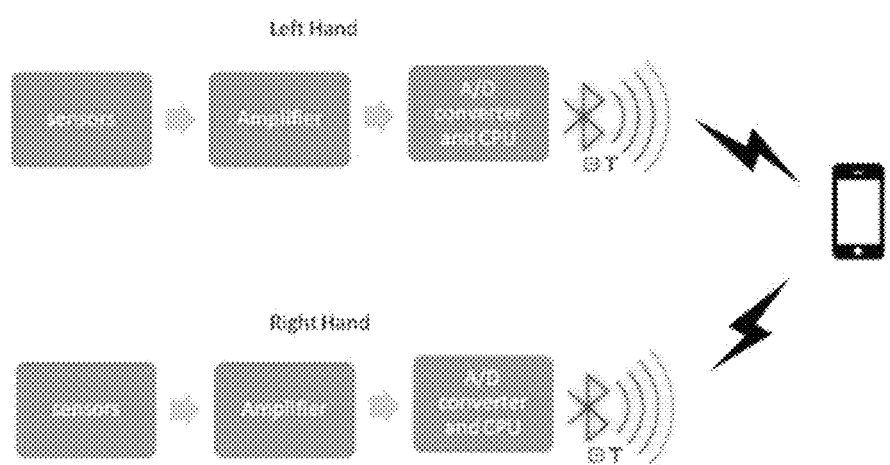
FIG. 3 is a block diagram illustrating hardware of the present invention, where a battery operated electronic device, mounted on each hand communicates with a mobile device.

FIG. 3 illustrates a block diagram of a system, comprising a battery operated electronic device mounted on each hand communicates with a mobile device. The battery operated electronic device on each hand includes sensors, an amplifier, an analog to digital converter, a microprocessor (CPU), and a Bluetooth modem. The mobile device has a program stored thereon that processes the information that it receives from the two wirelessly communicating electronic devices mounted on the hands. A program subroutine displays the GUI as shown in FIG. 1. Finally, a subroutine is configured to display an avatar or a short video and or produce alternative output signals.

Figure 4:
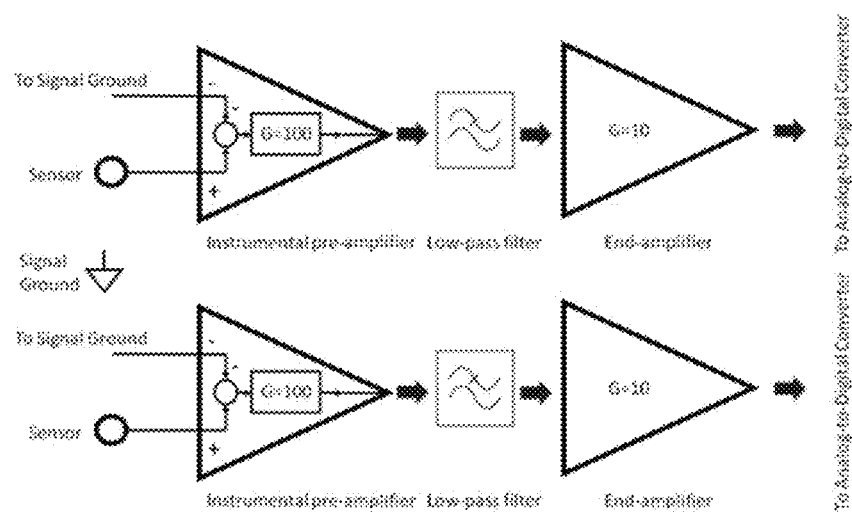
FIG. 4 is a diagram of a differential amplifier having two sensors and is connected to a ground.

FIG. 4 is a circuit diagram of part of the connection between sensors placed on the hands and a signal processor, illustrating an instrumental amplifier. In an example embodiment, the instrumental amplifier comprises two differential amplifiers and the two differential amplifiers are used on each hand. Each amplifier in FIG. 3 comprises two differential amplifiers as shown in FIG. 4. Instrumental pre-amplifiers have a gain of 100 and end amplifiers have a gain of 10. Total gain is 1000. Each amplifier is Two sensors and is connected to a ground. The ground electrode may be located on the wrists (wrist) under the boxes (box).

Figure 5:
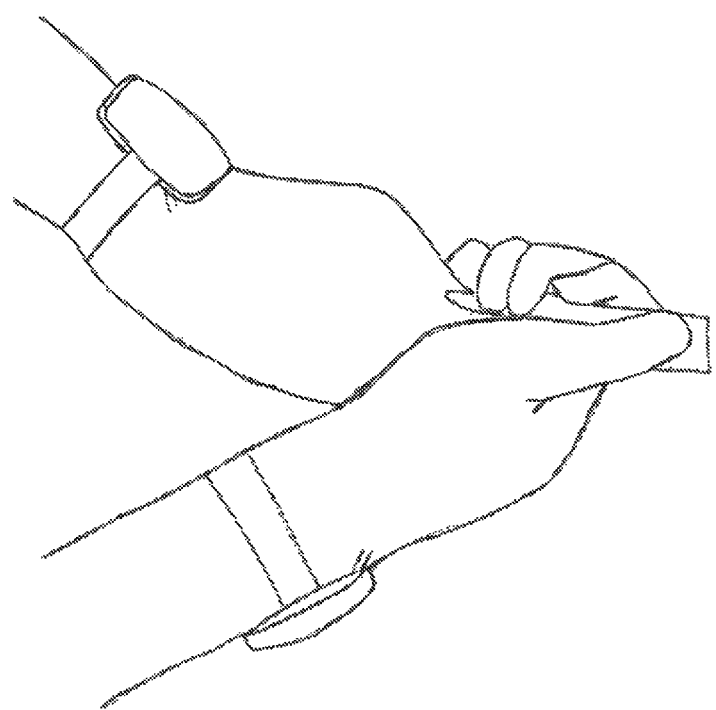
FIG. 5 illustrates two hands wearing gloves of the present invention and holding a golf club. Two wireless electronic boxes are attached to the wrists. Wires are also shown from boxes to electrodes inside of the gloves.
Figure 6:
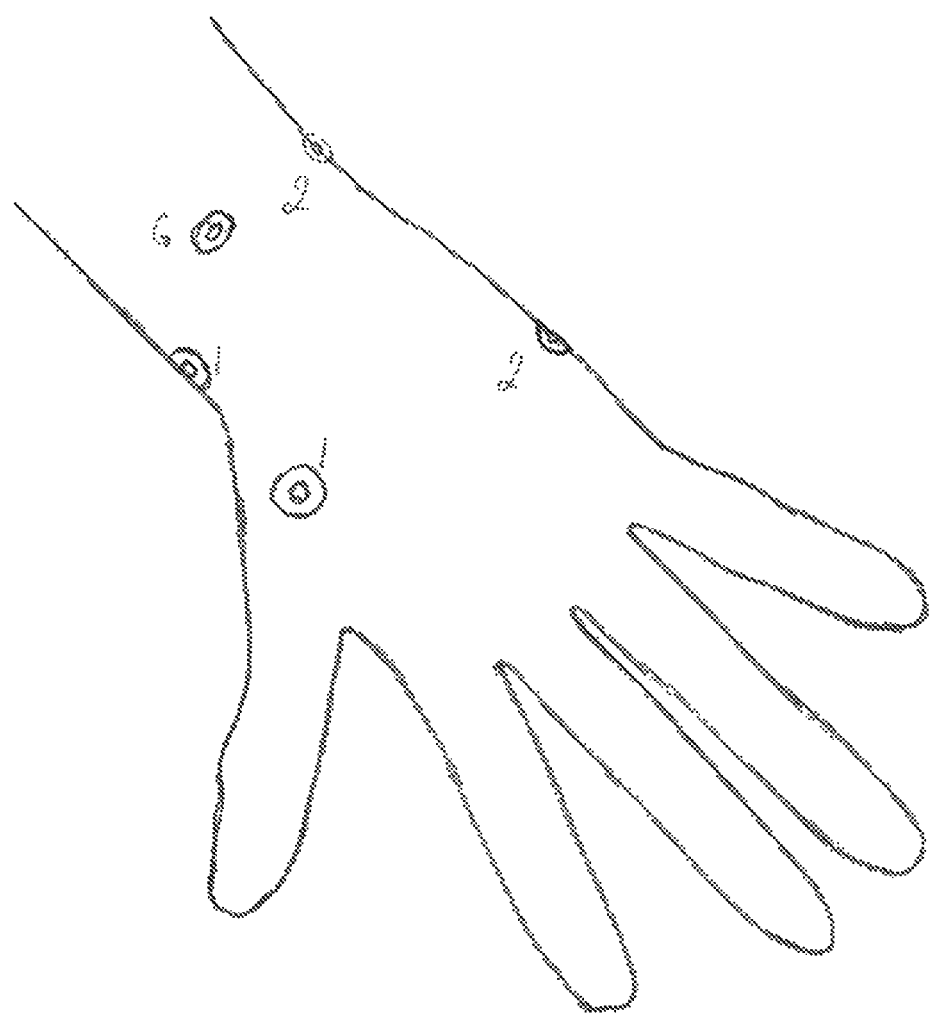
FIG. 6 illustrates a right hand, and placement of two pairs of differential electrodes. One of the differential electrodes is located on top of the skin over a muscle and another differential electrode is located on a bonny part of the wrist.
Figure 7:
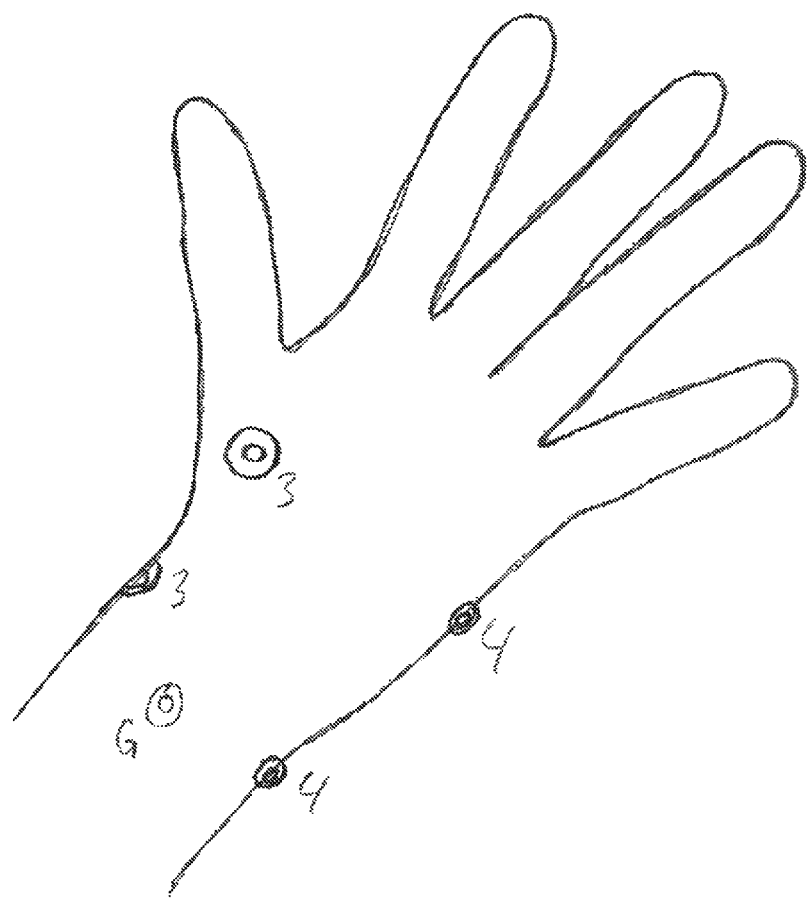
FIG. 7 illustrates a left hand, and placement of two pairs of differential electrodes. One of the differential electrodes is located on top of the skin over a muscle group and another differential electrode is located on a skin over a bonny part of a wrist.
Figure 8:
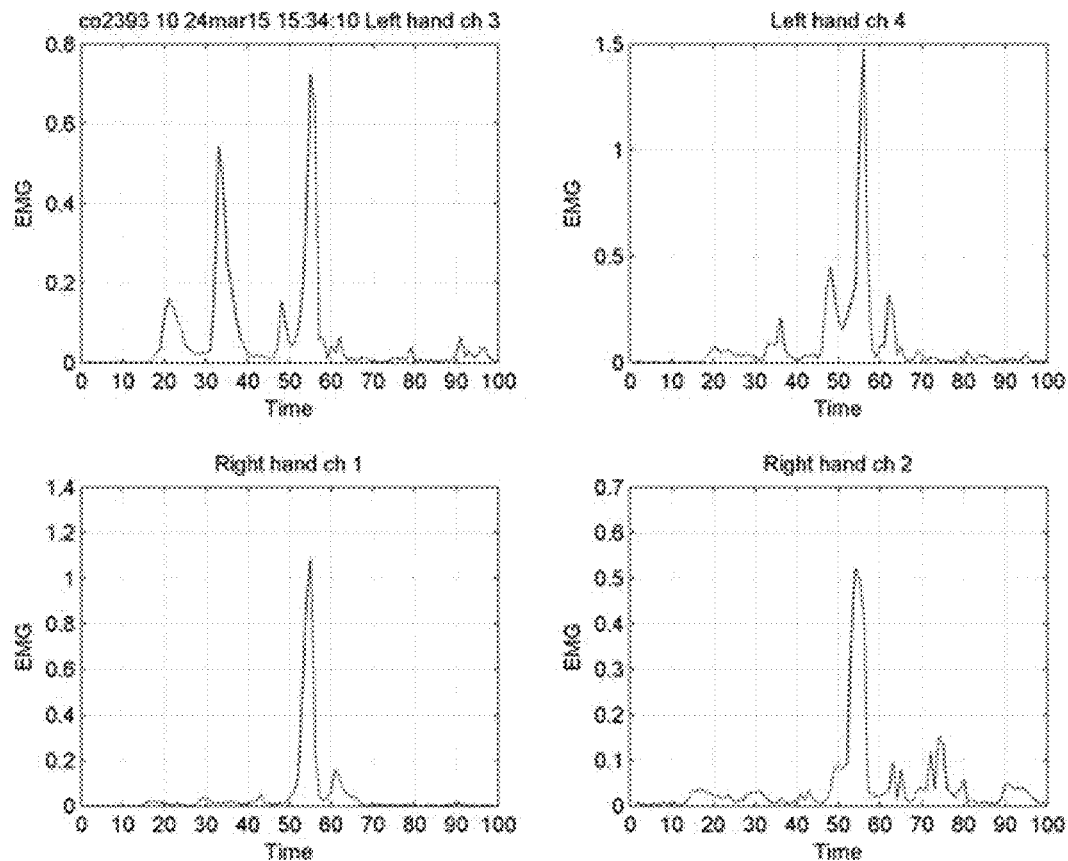
FIGS. 8 and 9 illustrates EMG activity of hand muscles during a golf swing of golf professionals.
Figure 9:
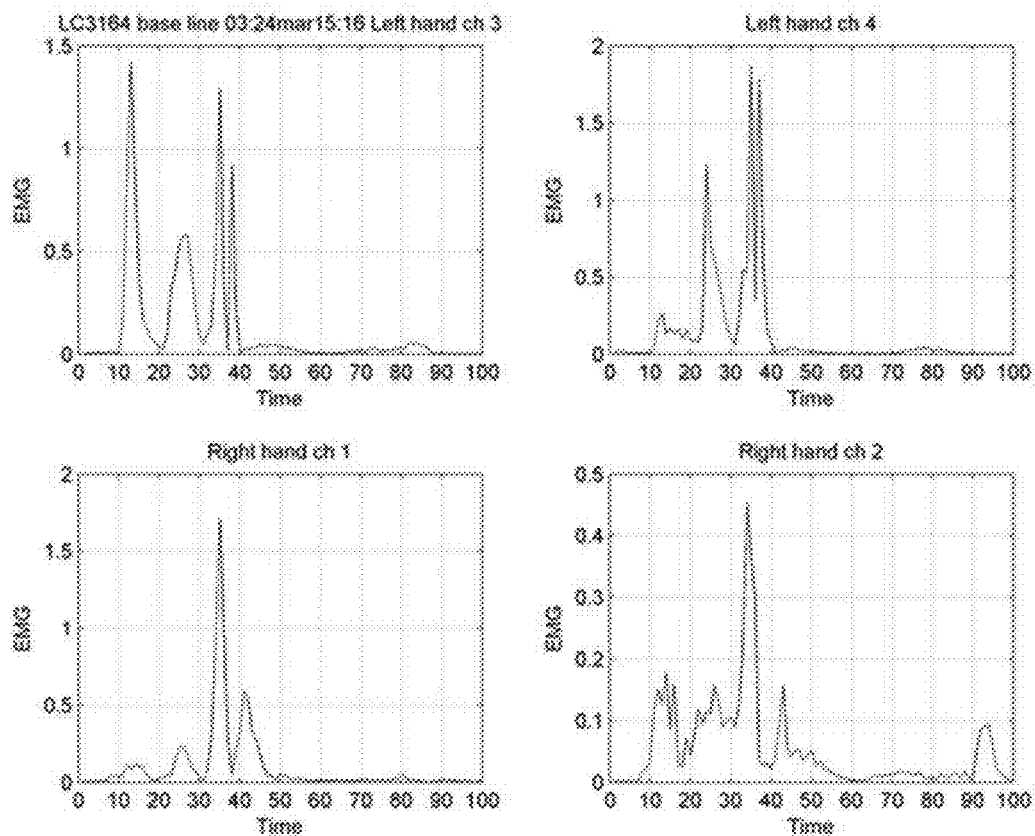
Figure 10:
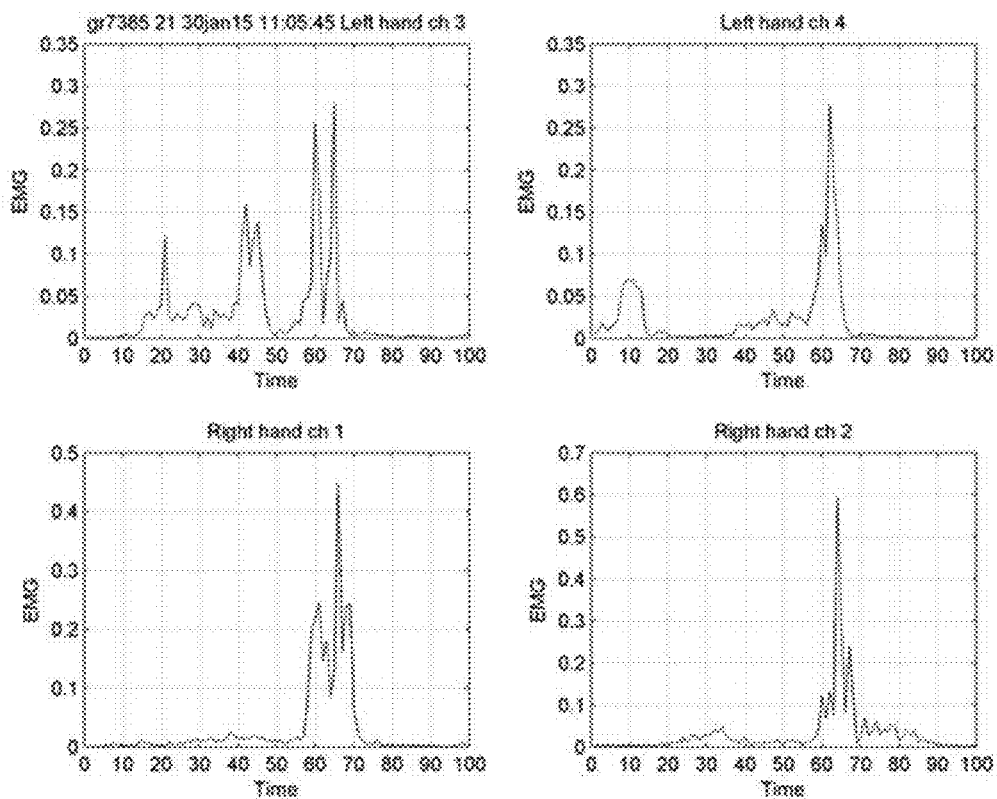
FIG. 10 illustrates EMG activity of a 15 year old boy after 30 minutes of training with the a golf training system of the present invention. However, this pattern was not always generated. In order for this pattern to appear more often, more training will be required to improve the coordination.
Figure 11:
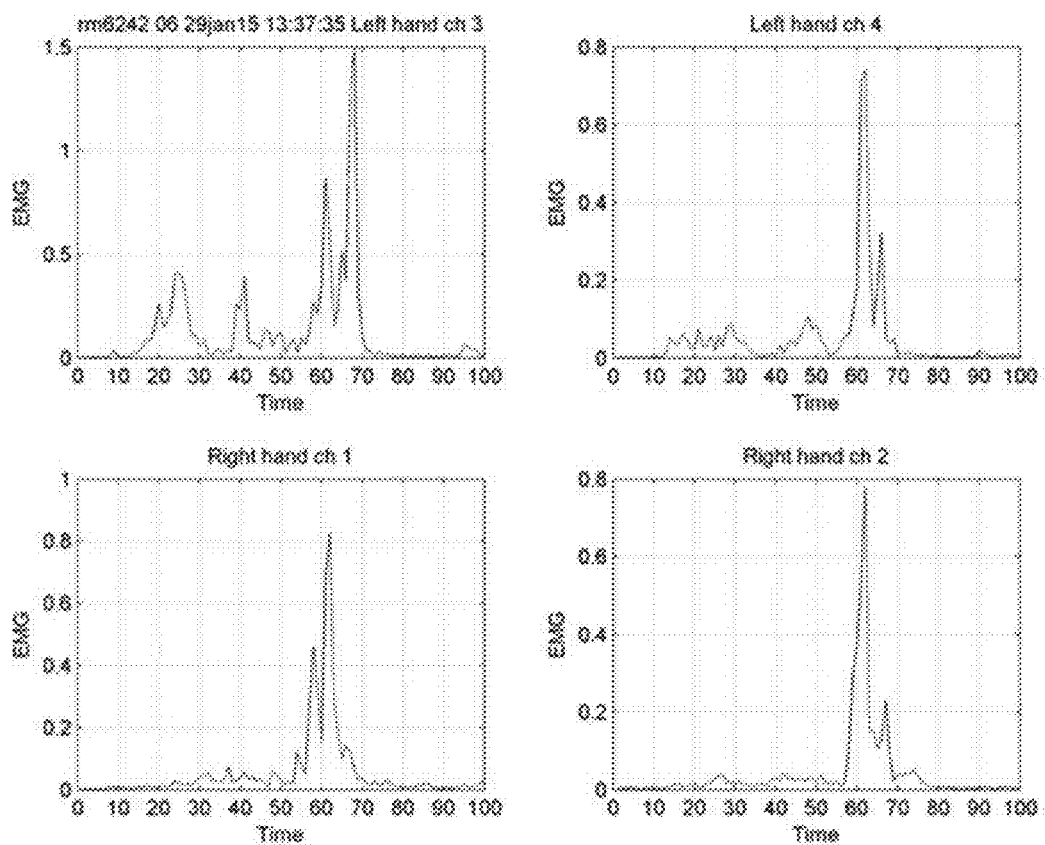
FIG. 11 illustrates EMG activity of a 16 year old girl after 30 minutes of training with the a golf training system of the present invention.
Figure 12:
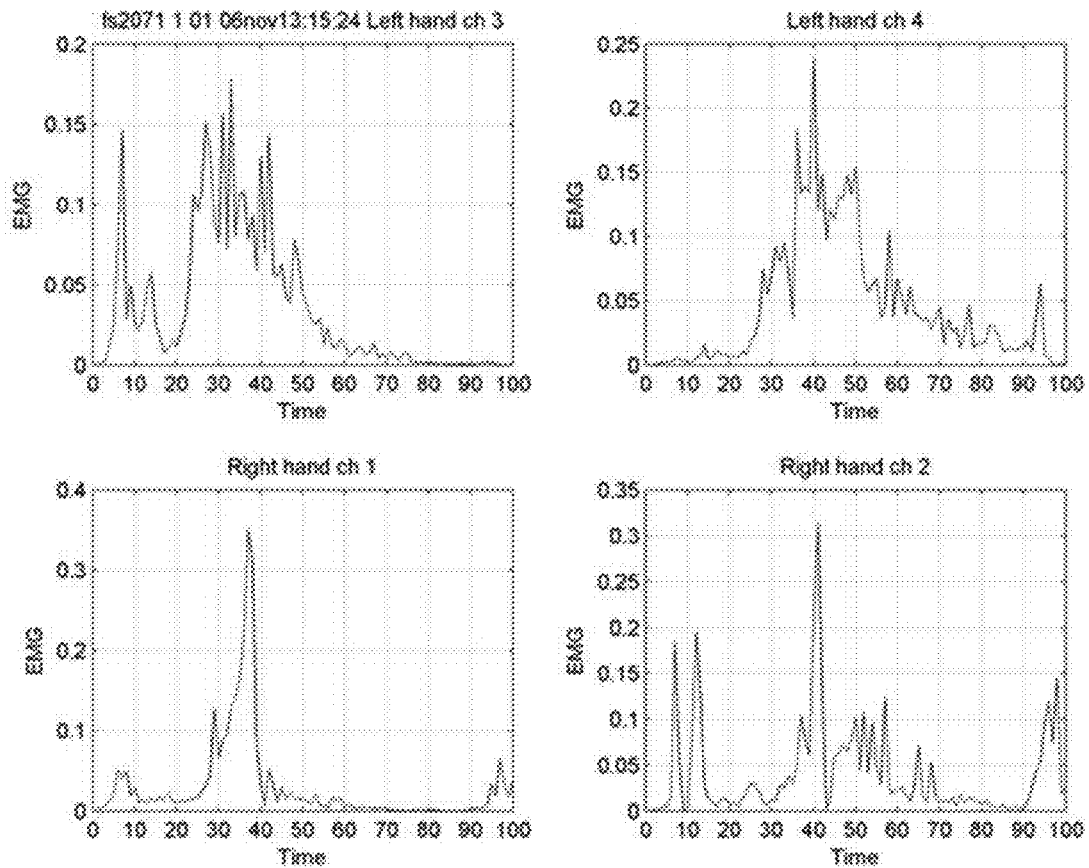
FIG. 12 illustrates EMG activity of a golf player on a university golf team with 10 years golf experience. This subject was not trained using our device. The common pattern was never found in his golf swings.

FIG. 5 illustrates two hands wearing gloves and holding a golf club. Wireless electronic boxes are attached to the wrists via bands. A set of wires connects the boxes to the gloves. Wires are connected to the gloves using connectors. Wires can be connected individually via external contacts, or can be embedded into the gloves. Inside the gloves, surface electrodes or sensors are disposed in predetermined locations. FIGS. 6 and 7 illustrate placement of electrodes inside the gloves that correspond to the muscle groups discussed earlier.

FIG. 6 illustrates a right hand, where two pairs of the differential electrodes are also shown. One differential electrode is located on a muscle and another on a bonny part of the wrist. FIG. 7 illustrates a left hand, where two pairs of the differential electrodes are also shown. One differential electrode is located on a muscle and another on a bonny part of the wrist.

In one example embodiment, surface EMG signals are recorded using an EMG recording device with a 1000 Hz sampling rate and 15-500 Hz filtering range. Commercial off the shelf adhesive disposable electrodes or dry Ag—AgCl electrodes may be used. Referring FIGS. 5-7, a user wears surface EMG electrodes, held in place by gloves on both left and right hands. Four EMG channels are recorded. Channels 1 and 2 correspond to the dominant hand, (in this example, the right hand), and channels 3 and 4 correspond to the non-dominant hand, (in this example, the left hand). Surface electrodes are placed over the thenar eminence, which allows compound EMG to be recorded from the flexor pollicis brevis and abductor pollicis brevis (channels 1 and 3), and over the hypotrhenar eminence, covering abductor digiti minimi, and flexor digiti minimi brevis (channels 2 and 4).

In order to see the changes in raw EMG (in units of millivolts) data more clearly, the following signal processing are conducted.

1. Compute Intensity by squaring the raw EMG value for voltage=$EMG^2$

2. Divide 4 second trials into 40-millisecond time intervals.

3. Compute mean intensity in each of the 100 intervals. The above computations may be made in a program running in CPUs shown on FIG. 3. The results of these computations may be transmitted to a computer device with the display.

Referring to FIG. 1, the sequence of moves in a golf swing is divided into seven movements numbered 1-7: 1) take away; 2) back swing; 3) down swing; 4) impact; 5) follow through; 6) finish; 7) watching.

Figure 2:
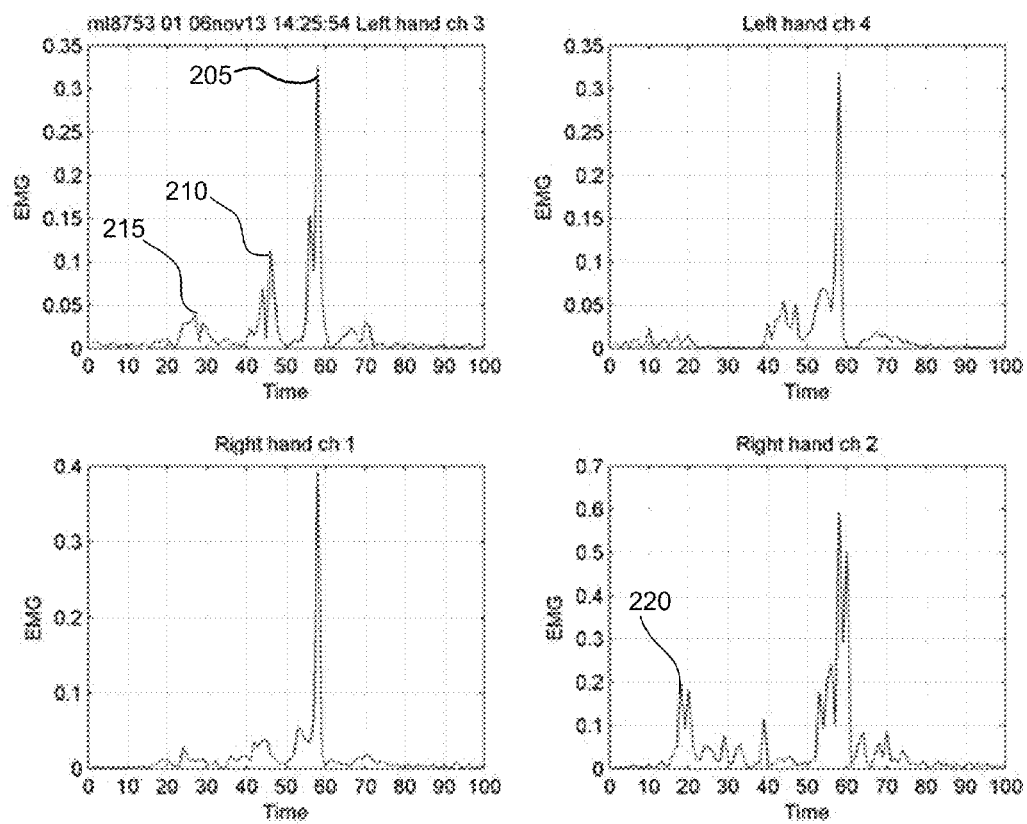
FIG. 2 illustrates EMG activity of a five time LPGA champion and golf professional, plotting energy in millivolt (my) squared versus time interval. This subject did not have the training with our device and she was swinging the club (5 iron) without trying to achieve her top performance.

EMG mean intensities that result from signal processing are shown on a chart as in FIGS. 2 and 8-12. FIG. 2 illustrates a chart for a golf teaching professional. The charts shown in the FIGS. 2, 8-12 comprise four graphs showing a relationship between EMG intensity in millivolts (my) squared and time expressed in time intervals. In FIG. 2, a clear sequence of EMG peaks can be observed. Between the peaks EMG activity is low. Moreover, the peaks are coordinated across the muscles of the right and left hands, as evident from the comparison of the time of the peaks. Additionally, note the presence of an early EMG peak in the right hand, which are not present in the left hand and vice versa. The chart of the golf teaching professional in FIG. 2 is used as a template for teaching users and students to achieve similar looking charts. In order to produce charts similar to FIG. 2, the present invention is employed. However, this subject was not trying to generate a particular pattern of intensities. She was just swinging a golf club (#5 iron) without even trying for her best performance.

The present invention provides an output after every swing (trial). This information could be interpreted to provide instructions to students on what is incorrect with their swing mechanics, by identifying which move of the separate movements in FIG. 1, is broken. To be clear, the users do not have to look at intensity charts. A computer program translates the intensity peaks and maps them to athletic moves in FIG. 1. Then, the program analyzes the parameters of the peaks and adds interpretations to the resulted athletic moves. In general, the present invention can be used to analyze the exact moves in every sequence of a complex movement and then teach them to a student. This invention may be used to teach how to control athletic movements. The present invention is not limited to a particular set of moves, but can be used to study the mechanics of any sequence of moves. After being taught to a student, the present invention is used to verify that the same moves were performed correctly.

Mean intensity is calculated in all 40-ms time intervals with zero corresponding to movement sequence onset. Intensity peak around 15 to 20 time intervals in channel 2 correspond to movement 1 of the right hand in take away swing shown in FIG. 1. Intensity peak around 20-30 time intervals in channel 3 correspond to the movement 2 of left hand in the back swing in FIG. 1. Intensity peak around 40-50 time intervals in channel 3 corresponds to the movement 3 of the left hand in down swing in FIG. 1. Intensity peak around 50-60 time intervals in channel 3 corresponds to the movement 4 (impact) of left hand in impact in FIG. 1. The intensity peak that corresponds to impact move is very similar in all four channels.

Determining whether an EMG pattern detected during a movement matches or does not match a reference pattern acquired from a professional may be carried out by the following method.

In the following steps, peak location and width may be found by utilizing known data analysis techniques and commercially available tools. Reference is made to FIG. 1 for identification of the movements and FIG. 2, as an example of EMG signals generated by the movements. A movement comprises the motion that begins with pose depicted at the tail of the arrow and ends with the pose depicted at the head of the arrow. An X displayed over an arrow associated with a movement indicates an incorrect movement, for example, as shown in FIG. 14. Any indicator may be used, however, the following examples employ an X to indicate an error with a specific move as whole, or with a specific hand during move or a specific muscle on a specific hand during a move.

Figure 15:
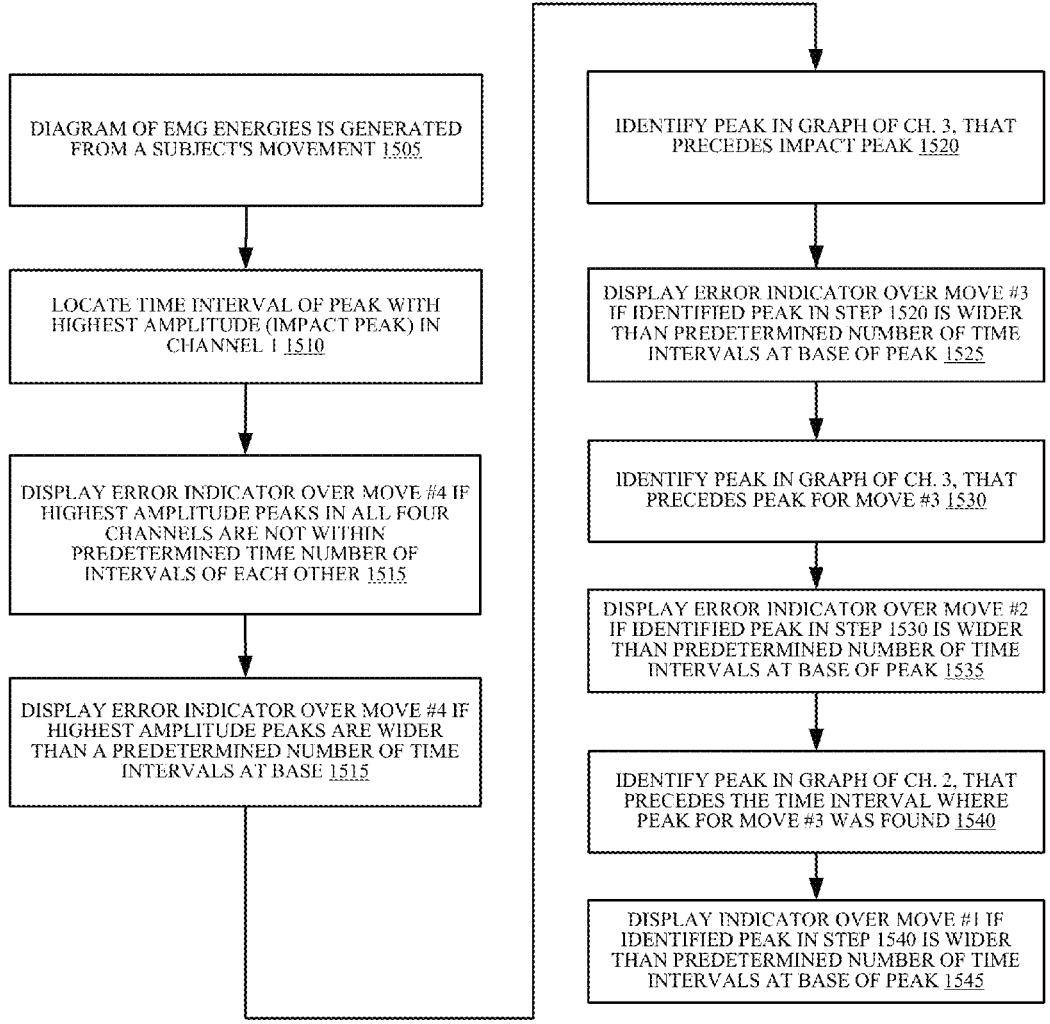
FIGS. 15 and 16 are flow charts of processes for identifying an incorrect athletic movement.

In a step, referring to FIG. 15, a diagram of EMG energies is generated from a subject's movement 1505, for example, shown in FIG. 2. In this case, a golf club swing, in a step, the intensity peak for move four 205 is found and the diagram of intensities is analyzed and the impact peak with the highest amplitude in channel 1, which is attached to the user's dominant hand, is identified. Since this peak corresponds to the club hitting the ball (impact), this peak should correspond to the highest amplitude peak during one trial in channels 2, 3, and 4. An X is displayed if all four peaks in four channels did not occur within plus or minus 5 time intervals of each other 1510. An X is displayed if the width at the bottom of the peak is more than 15 time intervals 1515.

In a step 1520, the intensity peak for move three 210 is identified. The diagram of intensities in channel 3 is analyzed and the peak immediately preceding (to the left of) the impact peak (precedes the impact peak) in that channel is identified. The X is displayed if the width at the bottom of the peak is more than 15 time intervals 1525.

In a step 1530, the intensity peak for move two 215 is identified. The diagram of intensities in channel 3 is analyzed and the peak immediately preceding (to the left of) the peak for move three is identified. An X is displayed if the width at the bottom of the peak is more than 15 time intervals 1535.

In a step 1540, the intensity peak for move one 220 is identified. The diagram of intensity in channel 2 are analyzed, and the peak immediately preceding (to the left of or backward in time from) the time interval found to be where the peak for move 2 was found. An X is displayed if the width at the bottom of the peak is more than 15 time intervals 1545. The number of time intervals of 5 and 15 are preferred, based on research to date, however, other predetermined time intervals can be substituted if further research indicates.

Figure 16:
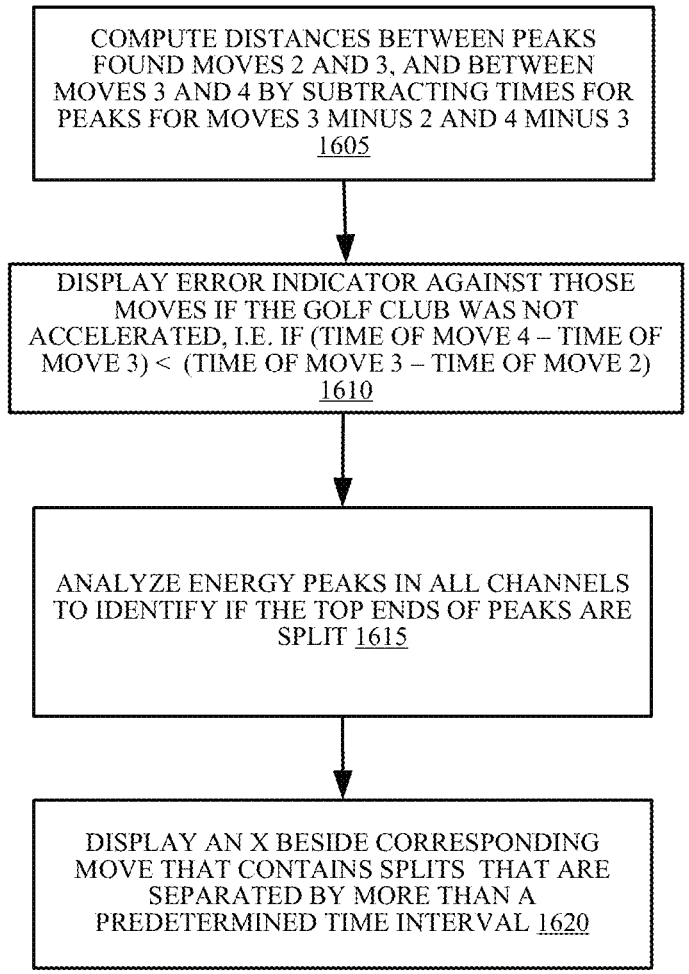

Referring to FIG. 16, in step 1605, intensities from channel 3 are analyzed. The distances between peaks found in moves 2 and 3, and between moves 3 and 4 are computed. Thus the times for peaks for moves 3 minus 2 and 4 minus 3 are compared. The distance (number of time intervals) between peaks in channels 2 and 3 should be greater than the number of time intervals between peaks in channel 3 and 4. This indicates that the golf club was accelerated and is a correct movement. X's are displayed against those moves if the golf club was not accelerated 1610.

In a step 1615, the intensities in all channels are analyzed for identifying if the top ends of a single peak are split into two distinct peaks. The presence of a split peak indicates information about varying strength of the grip of the club during the swing (regripping). X is displayed beside corresponding moves that have peaks with split peaks separated by less than a predetermined time interval 1620. If the split produces two separate peaks, for example, on FIG. 10, channel 3 in the area before and after 60 time intervals, this is an incorrect move and should be marked with an X.

If in any step, there is an absence of a peak, an X is displayed below the corresponding expected move. X is also displayed if the intensity peak occurs late in time.

If there is no intensity peak with the amplitude of at least 0.2 my in any channel, e.g. there is no impact intensity peak in any channel, or all peaks happened during different time intervals, an X is displayed under movement 4 in FIG. 1.

If there is no intensity peak to the left of the impact peak (movement 4) within at least 20 time intervals from the center of peak associated with movement 4, in channel 3, an X is displayed under movement 3.

If there is no intensity peak to the left of the peak corresponding to movement 3 within at least 30 time intervals from the center of the peak associated with movement 3, in channel 3, an X is displayed under movement 2.

If there is no intensity time peak of at least 0.1 my within the first 30 time intervals in channel 2, then put an X under move 1.

Optionally, the method includes steps for evaluating the quality of moves from the shapes of intensities, where the intensity is the average of $EMG^2$. Channel 1 and channel 2 are located on the dominant hand (e.g. right hand for a right handed person). Channels 3 and 4 are located on the non-dominant hand (e.g. left hand). In any of the above described steps, if an error message is displayed, it is displayed according to the hand and part of the hand the measurement originated from. Thus, the system observes where the correct and incorrect peaks are located by determining which channels and on which hands the error took place on. Optionally, the systems displays two hands holding a golf club in golf grip. The hands have colored spots, placed where the electrodes are positioned, generally top and bottom of each hand. A user taps on one hand or another and an image representation displays with only one hand. This hand has one of two color codes displayed (green or red) at the top or bottom. These color codes show hard grip or optimal, for example.

The system displays incorrect moves, as shown in FIG. 14, for example. If the width of the peak is too large, this means that he gripped too long. Optionally, the system is configured to display an explanation and video of a professional swinging slowly, if a user clicks on the move with an X, or another error indicator. The user then repeats the whole sequence.

A preferred method of analysis of the EMG graphs is described above. However, additional analysis is also possible. Optionally, different goals are set for players of different experience. The system optionally, vary the tolerable widths of intensity peaks, or their positions in time intervals. Some mistakes can be tolerable for less experienced players, but not acceptable for an experienced player. Thus, the system may be tuned to the style of individual players.

The present invention allows for further research in optimization of the metrics such as the differences between peaks in time intervals and the amplitudes of the peaks, and proportions of peaks amplitudes for different players at different levels. Different players can have different optimum proportions between the amplitudes of their peaks.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated. In addition, when a single callout line in the drawings leads to two or more separate reference numbers (first, second, etc. reference numbers), (and each reference numeral refers to a different piece of text in the detailed description) and it would be inconsistent to designate the drawing item being called out as both pieces of text, the drawing be interpreted as illustrating two different variants. In one variant, the drawing item is referred to by the first reference number and in another variant the drawing item is referred to by the second reference number, etc.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A training aid for an athletic movement, comprising:
an EMG acquisition device for placement on a muscle of a user; and
a processor and a computer readable medium, having computer readable instructions stored thereon, wherein when read by the processor, cause the processor to:
identify an acquired set of EMG signals generated during the movement from muscles in two different appendages;
divide the set of EMG signals into a sequence of smaller time intervals;
compare the placement in the smaller time intervals of peak EMG signals in the acquired set of EMG signals to a reference criteria;
identify whether the acquired EMG signals satisfy or does not satisfy the reference criteria during the movement;
display a set of movements that are matched to the acquired EMG set such that a displayed movement is matched to acquired EMG signals during one of the smaller time intervals, and the movements are displayed with an indication of which move or moves are wrong based on whether the EMG signals matched with the movement satisfies the reference criteria.

2. The training aid of claim 1, wherein the set of movements comprise a series of movements, that when aligned together in time, comprise the athletic movement with the indication of which of the series movements are wrong based on whether the EMG signals matched with the movement satisfies the reference criteria.

3. The training aid of claim 2, wherein identifying whether the acquired EMG signals satisfy or does not satisfy the reference criteria during the movement comprises identifying an intensity peak associated with a shorter movement and determining if the time interval of the peak is longer than a predetermined length of time; wherein if the time interval exceeds the predetermined time, the training aid displays an indication of error.

4. A training aid for completing a golf swing, comprising:
an EMG acquisition device for placement over a muscle in a hand of a user; and
a processor and a computer readable medium, having computer readable instructions stored thereon, wherein when read by the processor, cause the processor to:
identify an acquired pattern of EMG signals generated during the movement;
compare the acquired pattern to a reference EMG criteria;
display an indication of whether the acquired EMG pattern satisfies the reference EMG criteria during the movement.

5. The training aid of claim 4, wherein duration of the golf swing is divided into a sequence of movements, at least some of which are identified by the presence of EMG signal peaks in the acquired EMG pattern.

6. The training aid of claim 5, wherein one of the sequence of movements comprises an impact movement, and the training aid further comprises four EMG acquisition channels configured to acquire EMG signal patterns from two muscles in a dominant hand of the user and two muscles from a non-dominant hand of the user;
   wherein comparing the acquired pattern to a reference EMG criteria, comprises:
   first identifying a largest EMG signal peak acquired from each channel and determining whether the peak in each of the four channels occurred within a predetermined time interval of each other; and
   if all peaks did not occur within the predetermined time interval, displaying an indication that the EMG pattern failed to satisfy the reference EMG criteria for the impact movement.

7. The training aid of claim 6, wherein if any of largest EMG signal peaks occurred over a duration longer than a second predetermined time interval, displaying an indication that the EMG pattern failed to satisfy the reference EMG criteria.

8. The training aid of claim 7, wherein comparing the acquired pattern to a reference EMG criteria, comprises identifying a third EMG signal peak acquired immediately preceding the largest EMG signal peak; and
   if the third EMG signal peak occurred over a duration longer than a third predetermined time interval, displaying an indication that the EMG pattern failed to satisfy the reference EMG criteria, for a third movement immediately preceding the impact movement.

9. The training aid of claim 8, wherein comparing the acquired pattern to a reference EMG criteria, comprises identifying a second EMG signal peak acquired immediately preceding the third EMG signal peak; and
   if the third peak occurred over a duration longer than a fourth predetermined time interval, displaying an indication that the EMG pattern failed to satisfy the reference EMG criteria, for a second movement immediately preceding the third movement.

10. The training aid of claim 9, wherein comparing the acquired pattern to a reference EMG criteria, comprises identifying a first EMG signal peak acquired immediately preceding the second EMG signal peak, and from a channel configured to acquire EMG signals from the dominant hand of the user; and
    if the first peak occurred over a duration longer than a fourth predetermined time interval, displaying an indication that the EMG pattern failed to satisfy the reference EMG criteria, for a first movement in the sequence of movements comprising the golf swing.

11. The training aid of claim 10, wherein comparing the acquired pattern to a reference EMG criteria, comprises determining whether a duration of time between the third and fourth EMG signal peaks is shorter than a duration of time between the second and third EMG peaks; if the duration of time between the third and fourth EMG signal peaks is longer than a duration of time between the second and third EMG peaks, displaying an indication that the EMG pattern failed to satisfy the reference EMG criteria, for second, third and the impact movements comprising the golf swing.

12. The training aid of claim 8, wherein identifying a third EMG signal peak acquired immediately preceding the largest EMG signal peak, comprises identifying a third EMG signal peak acquired immediately preceding the largest EMG signal peak acquired in the user's non-dominant hand detected from a muscle connected to a thumb.

13. The training aid of claim 9, wherein the second EMG signal peak acquired immediately preceding the second EMG signal peak is acquired from the user's non-dominant hand detected from a muscle connected to a thumb.

14. The training aid of claim 10, wherein the channel configured to acquire EMG signals from the dominant hand of the user is configured to acquire EMG signals from a muscle connected to a little finger of the dominant hand.

15. The training aid of claim 4, wherein the processor is configured to:
    compute intensities of the based on acquired EMG signals;
    divide an entire time of the golf swing into a plurality of smaller equal length time intervals; and
    compute a mean intensity in each of the plurality of smaller time intervals.

16. A training aid for improving a golf swing, comprising:
    sensors for measuring electrical activity in muscles of both hands of a user;
    a processor configured to:
       divide the electrical activity into a sequence of time intervals;
       compare peak electrical activity detected by the sensors to a set of reference conditions of electrical activity for a sequence of movements that comprise a golf swing;
       cause a display device to identify which, if any, of the sequence of movements that comprises the golf swing, failed to meet the reference conditions;
       cause the display device to display the set of movements with the indication of which moves were wrong from the point of muscle activities.

17. The training aid of claim 16, wherein the reference conditions comprise a fourth peak electrical activity in both hands occurring within a predetermined time interval and if the peak electrical activity failed to occur within the predetermined time interval, the processor is configured to display an indication of a failed condition associated with at least one of the sequence of movements.

18. The training aid of claim 17, wherein the reference conditions comprise locating a third peak electrical activity occurring before the fourth peak electrical activity in a non-dominant hand of a user, and determining whether the third peak occurred over a duration shorter than a second predetermined time interval; if the third peak occurred over a duration longer than the second predetermined time interval, the processor is configured to display an indication of a failed condition for at least one of the sequence of movements.

19. The training aid of claim 18, wherein the reference conditions comprise locating a second peak electrical activity occurring before the third peak electrical activity in a dominant hand of a user, and determining whether the second peak occurred shorter than the second predetermined time interval.

20. The training aid of claim 16, wherein the reference conditions comprise determining whether a third intensity peak occurred within a predetermined time interval from a center of a maximum peak and the processor is configured to display an indication of a failed condition associated with a movement preceding an impact movement.

* * * * *